United States Patent [19]

Portoghese

[11] Patent Number: 4,730,048

[45] Date of Patent: Mar. 8, 1988

[54] GUT-SELECTIVE OPIATES

[75] Inventor: Philip S. Portoghese, Falcon Heights, Minn.

[73] Assignee: Regents of the University of Minnesota, Minneapolis, Minn.

[21] Appl. No.: 809,051

[22] Filed: Dec. 12, 1985

[51] Int. Cl.[4] .................. C07D 489/06; C07D 489/00; A61K 31/485
[52] U.S. Cl. ........................................ 546/45; 546/44; 546/46; 562/560; 562/565
[58] Field of Search ............................. 546/45, 44, 46; 514/282

[56] References Cited

U.S. PATENT DOCUMENTS

| | | | |
|---|---|---|---|
| 3,320,262 | 5/1967 | Lewenstein et al. | 546/45 |
| 4,362,870 | 12/1982 | Portoghese | 546/44 |
| 4,401,672 | 8/1983 | Portoghese | 514/282 |
| 4,608,376 | 8/1986 | Pasternak | 514/282 |

FOREIGN PATENT DOCUMENTS

| | | | |
|---|---|---|---|
| 0077521 | 4/1983 | European Pat. Off. | 514/282 |
| 0018824 | 10/1966 | Japan | 546/46 |

OTHER PUBLICATIONS

D. R. Brown et al., *Neuropharmacology*, 24, 181–191, (1985).
L. M. Sayre et al., *J. Org. Chem.*, 45, 3366–68, (1980).
Bognar et al., Chemical Abstracts, vol. 71, 13243, (1969).
Jiang et al., Chemical Abstracts, vol. 87, 62629s, (1977).
Portoghese et al., Chemical Abstracts, vol. 90, 80864f, (1979).
Portoghese et al., Chemical Abstracts, vol. 92, 121619s, (1980).
Pasternak et al., Chemical Abstracts, vol. 93, 19120f, (1980).
Hahn et al., Chemical Abstracts, vol. 104, 102337y, (1986).
Remington's Pharmaceutical Sciences, A. Osol, ed., Mack Publishing Co., Easton, Pa., (16th ed., 1980), p. 395.
Sigma Price List 1987, Sigma Chem. Co., St. Louis, Mo., pp. 197–200.

*Primary Examiner*—Donald G. Daus
*Assistant Examiner*—Diana G. Rivers
*Attorney, Agent, or Firm*—Merchant, Gould, Smith, Edell, Welter & Schmidt

[57] ABSTRACT

Gut-selective agonist or antagonist opiates of the formula:

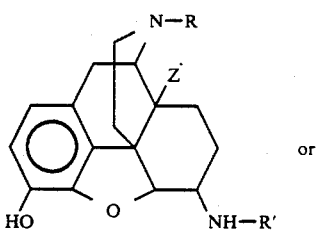

or

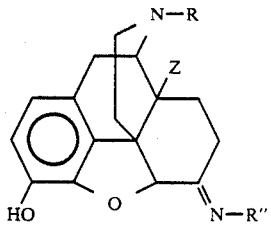

wherein R is $(C_1-C_5)$alkyl, $C_3-C_6$(cycloalkyl)alkyl, aryl, aralkyl or trans-$(C_2-C_5)$alkenyl; Z is H or OH, R' is (C=O)-A(B)(C) wherein A is selected from the group consisting of $(C_1-C_5)$alkyl, $(C_2-C_5)$alkenyl and $(C_2-C_6)$alkoxy (alkyl); B is selected from the group consisting of H, amino and a $(C_1-C_5)$alkyl group optionally substituted with $CO_2H$, OH or phenyl and C is $CO_2H$, $SO_3H$, amino or guanidino; and R" is selected from the group consisting of NH-A(B)(C) or is guanidino; and the pharmaceutically-acceptable salts thereof.

4 Claims, No Drawings

GUT-SELECTIVE OPIATES

BACKGROUND OF THE INVENTION

It has long been known that the naturally-occurring semisynthetic opium alkaloids, or "opiates", manifest their pharmacologic effects both centrally and peripherally. The primary target sites for the former effects are the brain and the spinal cord. For example, morphine is used as an analgesic, to induce sleep in the presence of pain and to suppress cough. The major peripheral sites are located in the gastrointestinal tract. Thus, opiate agonists also inhibit gastric emptying and the propulsive motor activity of the intestine. The antidiarrheal action of opiate analgesics such as morphine is a manifestation of this effect. Efforts to minimize the central nervous system (CNS) effects of opiates while retaining a useful level of activity in peripheral tissues have resulted in the preparation of quaternary derivatives of narcotic antagonists and agonists by addition of a second alkyl substituent on the ring nitrogen atom. See D. R. Brown et al., Neuropharmacology, 24, 181 (1985). However, while these compounds generally exhibit reduced penetration of the blood brain barrier, they also exhibit a substantially-lowered overall affinity for opiate receptors.

Therefore, a need exists for opiates which exhibit high levels of activity with respect to gastrointestinal tissue, without exhibiting substantial levels of access to the CNS. A need also exists for opiates with characteristically high levels of antidiarrheal activity which exhibit low levels of undesirable CNS effects such as drowsiness, lowered respiratory activity and addictive potential. A further need exists for gut-specific antagonist opiates which can selectively reverse the peripheral activity or protect against the peripheral activity of agonist narcotics.

SUMMARY OF THE INVENTION

The present invention is directed to novel compounds of the general formulae I or II:

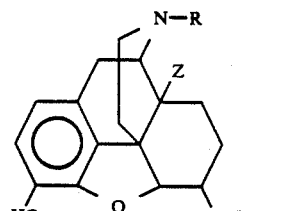

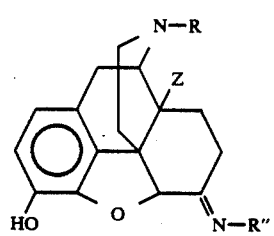

wherein R is $(C_1-C_5)$alkyl, $C_3-C_6$(cycloakyl) alkyl, acryl, aralkyl or trans-$(C_2-C_5)$alkenyl; Z is H or OH, R' is (C=O)-A(B)(C), wherein A is selected from the group consisting of $(C_1-C_5)$alkyl, $(C_2-C_5)$alkenyl and $(C_2-C_6)$alkoxy(alkyl); B is selected from the group consisting of H, amino and a $(C_1-C_5)$alkyl group optionally substituted with $CO_2H$, OH, or phenyl; and C is $CO_2H$, $SO_3H$ amino or guanidino; and R" is selected from the group consisting of NH-A(B)(C) or guanidino. Preferably, R is $(C_1-C_3)$alkyl, alkyl or cyclopropylmethyl, B is H or amino, and C is $CO_2H$ or guanidino.

Thus, preferred opiates of formula I are prepared by attaching hydrophilic, ionizable moieties R' and R" to the 6-amino group of naltrexamine [I: R=(cyclopropyl)methyl, Z=OH and R'=H] or oxymorphamine (I: R=$CH_3$, Z=OH and R'=H). The opiates of formula II can be prepared by converting the 6-keto-group of oxymorphone (III: R=$CH_3$, Z=OH) or naltrexone [III: R=(cyclopropyl)methyl, Z=OH] to the ionizable, hydrophilic group (R"N=) by a Schiff base reaction with a suitable amino-compound.

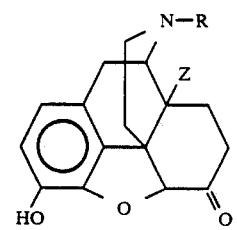

In a similar fashion, deoxy-opiates of formulae I and II wherein Z=H may be prepared from readily available starting materials, as described hereinbelow.

The configuration of the 6-(R'NH) group of formula I may be alpha- or beta- with respect to the plane of the cyclohexyl ring to which it is attached. Alternatively, the compounds of formula I may comprise mixtures of both configurations of the R'NH group.

Since the groups R'NH— and R"N= contain one or more acidic or basic substituents that contribute to the ability of molecule to substantially ionize at physiologic pH's or at the pH of the gut (pH 1-7), they are expected to confer low lipid solubility on opiates I and II, thereby minimizing their access to the CNS. Thus, the compounds of the present invention are expected to exhibit greater selectivity toward peripheral mammalian tissues such as gut tissue, and concomitantly lower CNS activity.

The agonist compounds of the present invention may be employed to modify intestinal function with minimal abuse potential or other CNS side effects when administered orally. Compounds in this series which are opiate antagonists could be used to selectively block the constipating effects of narcotic analgesics. Also, the compounds of the present invention may be useful to modulate endocrine and renal activity with minimal CNS action.

Therefore, the invention also comprises the pharmaceutically acceptable salts of the biologically-active opiates of formulae I and II, together with a pharmaceutically acceptable carrier for administration in effective non-toxic dose form. Pharmaceutically-acceptable amine salts may be salts of organic acids, such as acetic, lactic, malic, or p-toluene sulphonic acid, and the like as well as salts of pharmaceutically acceptable mineral acids, such as phosphoric, hydrochloric or sulfuric acid, and the like. Pharmaceutically-acceptable carboxylate salts of the present opiates may also be employed, e.g., amine salts, such as dimethylamine and triethylamine salt, the ammonium salt, tetrabutylammonium salt, cyclohexylamine salt, dicyclohexylamine salt; and metal salts, e.g., mono-, di-and tri-sodium salt, mono-, di- and tripotassium salt, magnesium salt, calcium salt and zinc salt.

These physiologically acceptable salts are prepared by methods known in the art. Metal salts can be prepared by reacting a metal hydroxide with the free acid. Examples of metal salts which can be prepared in this way are salts containing Li, Na, K, Ca, Mg, Zn, Mn and Ba. A less soluble metal salt can be precipitated from a solution of a more soluble salt by addition of a suitable metal compound. Thus for examples, Zn, Mg and Mn salts can be prepared from the corresponding sodium salts. The metal ions of a metal salt of a carboxylic acid can be exchanged by hydrogen ions, other metal ions, ammonium ion and ammonium ions substituted by one or more organic radicals by using a suitable cation exchanger.

In clinical practice, the opiates or the salts thereof will normally be administered orally or parenterally, by injection or infusion, in the form of a pharmaceutical preparation comprising the active ingredient in combination with a pharmaceutically acceptable carrier which may be a solid, semi-solid or liquid diluent or an ingestible capsule. The compound or its salt may also be used without carrier material. As examples of pharmaceutical preparations may be mentioned tablets, suspensions, liposomes, and the like. Usually the active substance will comprise between about 0.05 and 99%, or between 0.1 and 95% by weight of the preparation, for example between about 0.5 and 20% of preparations intended for injection and between about 0.1 and 50% of preparations intended for oral administration.

Other salts may be prepared and then converted by conventional double decomposition methods into pharmaceutically acceptable salts directly suitable for the treatment of diarrhea in mammals, or for the relief of constipation caused by opiate analgesics.

DETAILED DESCRIPTION OF THE INVENTION

The synthesis of representative compounds of formula I is outlined in Table I.

TABLE I

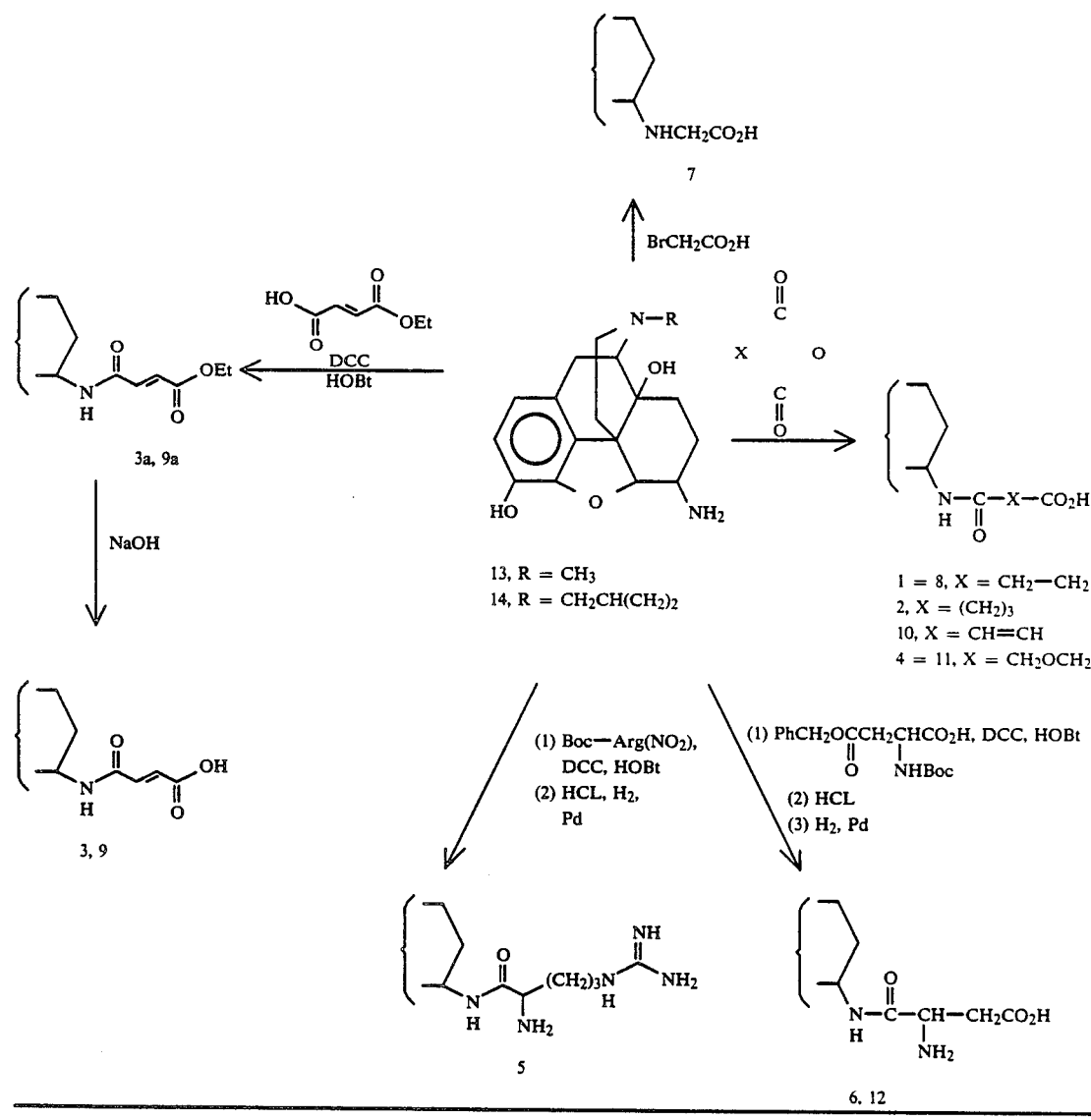

The starting materials 13 and 14 were prepared as described by L. M. Sayre et al., in J. Org. Chem., 45

3366 (1980), the disclosure of which is incorporated by reference herein.

Compounds 1, 2, 4, 8, 10 and 11 can be prepared by reaction of the parent 6-amino opiates 13 or 14 with the appropriate anhydride.

The carboxymethyl derivative 7 was prepared by reaction of bromoacetic acid ($BrCH_2CO_2H$) with 14 in the presence of a dialkylamine. Similarly, other (alpha-bromosubstituted)carboxylic acids would be expected to react with the 6-amino group of 13 or 14 to yield analogs of 13 or 14 substituted by an alpha-amino acid which is bound to the 6-position of the opiate via the alpha-amino group. Thus, the R'NH-substituent of 7 is a glyc-N-yl moiety. Other preferred R'HN- substituents introduced in this manner include alanin-N-yl, serin-N-yl, threonin-N-yl, valin-N-yl, leucin-N-yl, isoleucin-N-yl, phenylalanin-N-yl, tyrosin-N-yl, aspartic acid, N-yl, glutamic acid, lys-N-yl and arginin-N-yl, as well as other synthetic and naturally-occuring alpha-amino acids. Therefore, R'NH— is preferably a naturally-occurring "amino acid-N-yl radical".

The fumaramic acids 3 and 9 were prepared by coupling the half ester of fumaric acid ($HO_2CCH=CHCO_2Et$, Aldrich Chemical Co., Milwaukee, WI) with 13 or 14, respectively in the presence of dicyclohexylcarbodiimide (DCC) and hydroxybenztriazole (HOBt) to yield fumaramate esters 3a and 9a. The fumaramate esters were subjected to hydrolysis in an alcoholic solution of an alkali metal hydroxide such as ethanolic sodium hydroxide (NaOH).

The aspartyl esters 6 and 12, were obtained by coupling $PhCH_2O_2CCH_2CH(NHBoc)CO_2H$ (Chemical Dynamics Corp., South Plainfield, NJ) with 14 or 13 in the presence of DCC and HoBt, followed by deprotection with acid (HCl) to remove the Boc group and removal of the benzyl ($PhCH_2$) group by hydrogenolysis ($H_2$, Pd catalyst).

The arginyl derivative 5 was prepared by coupling $HO_2C-CH(NHBoc)(CH_2)_3NH(C=NH)NHNO_2$ (Boc-Arg($NO_2$)), Aldrich Chemical Co., Sigma Chemical Co., St. Louis, MO) with 13 in the presence of DCC and HOBt, followed by deprotection of the arginyl moiety with acid (HCl) and hydrogenolysis.

Opiates of formula I within the scope of the present invention can also be prepared from the starting material of formula I wherein and R=allyl, Z=OH and R'=H, which is prepared as described by J. B. Jiang et al., in J. Med. Chem., 20, 1100 (1977), the disclosure of which is incorporated by reference herein.

Opiates of formula I wherein Z=H can be prepared by reaction sequences analogous to those shown in Table I from starting materials such as I [R=(cyclopropyl)methyl, Z=H, R'=H] as disclosed by J. W. Schoenecker, Ph.D. Thesis, University of Minnesota, 1984, or I [R=$CH_3$, Z=H, R'=H] as disclosed by R. Bognar et al., Acta Chim. Acad. Scient. Hung., 58, 203 (1968), the disclosures of which are incorporated by reference herein.

Opiates of formula II can be prepared by reacting the 6-keto group of oxymorphone (III: R=$CH_3$, Z=OH) or naltrexone [III:R=(cyclopropyl)methyl, Z=OH] with hydrazine derivatives such as $H_2NNH(C_1-C_4)$alkyl-$CO_2H$ to form the corresponding hydrazones wherein R''=NH($C_1-C_4$)alkyl-$CO_2H$. Hydrazones of formula II were prepared wherein R=(cyclopropyl)methyl, Z=OH and R''=$NHCH_2CO_2H$ (15) or $NHC(=NH)NH_2$ (16) by reacting naltraexone-HCl with alphahydrazinoacetic acid and aminoguanidine, respectively.

Hydrazones of formula II wherein Z=H can be prepared analogously from starting materials such as hydromorphone (III: R=$CH_3$, Z=H; Mallinckrodt, Inc., St. Louis, MO) or opiate III [R=(cyclopropyl)methyl, Z=H], prepared as disclosed by M. Gates et al., J. Med. Chem., 7, 127 (1964), the disclosure of which is incorporated by reference herein. Hydrazones of formula II wherein Z=H and R=allyl can be prepared from naloxone (III: Z=H, R=allyl).

The invention will be further described by reference to the following detailed examples, wherein melting points were determined with a Thomas-Hoover capillary melting point apparatus and are uncorrected. Elemental analyses were performed by M-H-W Laboratories, Phoenix, Arizona. All analytical results were within ±0.4% of the theoretical values. IR spectra were recorded on a Perkin-Elmer 281 spectrophotometer. NMR spectra were recorded on either JNM-FX 90Q FT NMR spectrometer, or Nicolet 300 MHz NMR spectrometer with tetramethylsilane as internal standard. Mass spectra were obtained on an AEI M5-30 (EI, 20 eV) or Finnigan 4000 (CI, $NH_3$, positive or negative). All $R_f$ values were obtained on Analtech silica gel TLC plates.

EXAMPLE 1

Preparation of Compounds 1, 2, 4, 8, 10, 11

The appropriate acid anhydride (succinic, maleic, glutaric, or 3-oxyglutaric) (0.33 mmol) was dropped over a 1.0 hr period into a dimethylformamide (DMF) (2.5 ml) solution containing 0.33 mol of naltrexamine 14 or oxymorphamine 13. After stirring for an additional 3.0 hr at 25° C., the mixture was poured into ether (50 ml) and the precipitate was collected by filtration. Crystallization from acetone or aqueous acetone afforded the pure acids, 1, 2, 4, 8, 10, or 11.

EXAMPLE 2

Preparation of Fumaramic Acids 3 and 9

To a mixture of the dihydrochloride of 11 or 13 (0.62 mmol), triethylamine (TEA) (0.35 g, 2.48 mmol) and dimethylformamide (2 ml) that had been stirred at 25° C. for 15 min, was added fumaric acid monoethyl ester (0.089 g, 0.68 mmol) and 1-hydroxybenzotriazole (HOBt) (0.189 g, 1.24 mmol). Dicyclohexylcarbodiimide (DCC) (0.192 g, 0.93 mmol) was then added to the cooled mixture (0° C.) which was then stirred for 1.0 hr and at 25° C. for 10 hr. The reaction mixture was poured into water (50 ml) containing sodium carbonate, and the mixture was extracted with ethyl acetate (5×25 ml). After removal of the solvent in vacuo, the product was chromatoqraphed on silica gel (EtOAc-MeOH-$Me_3N$, 90:10:0.5) to afford the ethyl ester intermediates, 3a or 9a, respectively, which were hydrolyzed in ethanolic NaOH (0.5 N, 5 ml) at 25° C. for 10 hr. The mixture was adjusted to pH 8 with 1N HCl and the solvent was removed in vacuo. The product (3 or 9) was purified by chromatography on silica gel (EtOAc-MeOH-$NH_4OH$, 70:30:4).

EXAMPLE 3

Synthesis of Aspartic Acid Derivatives 6 and 12

A mixture of the dihydrochloride of 14 or 13 (0.67 mmol), triethylamine (0.38 g, 2.67 mmol), and dimethylformamide (2 ml) was stirred at 25° C. for 15 min. To this was added PhCH$_2$O$_2$CCH$_2$CH(NHBoc)CO$_2$H (0.237 g, 0.73 mmol) and 1-hydroxybenzotriazole (0.180 g, 1.33 mmol), and the mixture cooled to 0° C. Dicyclohexylcarbodiimide (0.206 g, 1 mmol) was then added, and stirring was continued at 0° C. for 1.0 hr and at 25° C. for 10 hr. The mixture was filtered and the filtrate was poured into water (50 ml) containing sodium carbonate (0.2 g). The product was extracted with ethyl acetate (EtOAc) (4×25 ml). After removal of the solvent in vacuo, the residue was treated with HCl to afford products (6 or 12, respectively) as the dihydrochloride salts.

EXAMPLE 4

β-Naltrexamineacetic acid (7)

β-Naltrexamine 2HCl (0.415 g, 1 mmol) was suspended in acetonitrile (7 ml) and diisopropylethylamine (0.61 g, 3.5 mmol) was added. After 10 min, bromoacetic acid (0.153 g, 1.1 mmol) was added and the reaction mixture was allowed to stand at 25° C. for 10 hr. After removal of solvent, the solid residue was recrystallized from hot isopropanol containing 1% MeOH to afford 0.265 g (66%) of 7, mp>280°.

EXAMPLE 5

Arginyl-β-naltrexamine (5).

β-Naltrexamine 2HCl (0.415 g, 1 mmol) was suspended in DMF (3 ml), and TEA (0.3 ml) was added. After cooling to 0° C., Boc-Arg(N0$_2$) (0.319 g, 1 mmol), HOBt (0.405 g, 3 mmol) and DCC (0.210 g, 1 mmol) were added. The reaction was stirred at 0° C. for 1.0 hr and at 25° C. for 12 hr. The mixture was filtered and washed with DMF (0.5 ml). To the filtrate, 10% aqueous NaHCO$_3$ (50 ml) was added, and the mixture was extracted with ethyl acetate (3×50 ml). The ethyl acetate was dried over magnesium sulfate and the solvent was evaporated in vacuo. The residue was triturated with ethyl ether, and the solid that formed was filtered and washed with ether. The nitroarginyl intermediate (0.610 g, 95% yield), mp 153°-156° C., was dissolved in 4N HCl in ethyl acetate (10 ml), and after 20 min, 10 ml of ethyl acetate was added. This solid was filtered and washed with ethyl acetate. Yield, 0.510 g (73%); mp 258° C. (dec); R$_f$=0.18 (nBuOH—AcOH—H$_2$O, 4:1:1).

Arg(NO$_2$)-β-naltrexamine 2HCl (400 mg, 0.57 mmol) was dissolved in methanol (15 ml) and 10% Pd/C catalyst (50 mg), and conc. HCl (0.3 ml) were added. After hydrogenation for 24 hr, the catalyst was removed by filtration and the solvent was evaporated in vacuo. The residual solid was precipitated by addition of EtOAc to afford 370 mg (96%) of 5, mp>280° C., R$_f$=0.12 (nBuOH-HOAc-H$_2$O).

EXAMPLE 6

Boc-α-hydrazinoacetic acid

To a cooled methanolic (40 ml) (0° C.) solution of NaOH (3.2 g, 0.08 mol) and Boc-hydrazine (5.3 g, 0.04 mol) was added bromoacetic acid (5.6 g, 0.04 mol) in methanol (10 ml). The solution was refluxed for 3.0 hr, 50 ml of water was added, and the mixture was extracted twice with ethyl acetate. The aqueous phase was acidified to pH 4 with citric acid (3.4 g), and extracted with ethyl acetate. The organic phases were collected and dried (MgSO$_4$). The solvent was removed by evaporation, and the resulting solid was washed twice with ethyl ether. Yield, 3.5 g (46%); mp 144°-146° C.; R$_f$=0.51 (nBuOH-H$_2$O-HOAc, 4:1:1).

EXAMPLE 7

α-Hydrazinoacetic acid

The Boc-α-hydrazinoacetic acid (1.90 g, 0.01 mol) was dissolved in 4N HCl in ethyl acetate (20 ml). The precipitate that formed was isolated by decantation and was triturated with ethyl ether. Yield, 1.25 g (100%); R$_f$=0.1 (nBuOH-H$_2$O-HOAc, 4:1:1).

EXAMPLE 8

Naltrexazoneacetic acid (15)

Naltrexone.HCl (0.377 g, 0.001 mol) was added to a methanol (2 ml) solution containing α-hydrazinoacetic acid (0.127 g, 1 mmol) and triethylamine (0.30 ml, 2.2 mmol), and the mixture was stirred for 12 hr at 25° C. The precipitate that formed was filtered and washed with methanol (0.5 ml), isopropanol (2 ml), and ethyl ether (2 ml). Crystallization from methanol afforded 0.274 g (66%) of 15, mp 340° (dec), R$_f$=0.21 (nBuOH-HOAc-H$_2$O, 4:1:1).

EXAMPLE 9

Naltrexazone iminosemicarbazone (16)

Aminoguanidine carbonate (138 mg, 1 mol) was suspended in ethanol (25 ml) containing concentrated HCl (0.1 ml), and the solvent was removed. The residual solid was dissolved in ethanol (50 ml), naltrexone.HCl (377 mg, 1 mmol) was added, and the mixture was heated under reflux for 0.5 hr. The solid product was collected by filtration and washed with hot ethanol to afford 451 mg (96%) of 16%. R$_f$=0.39 (nBuOH-HOAc-H$_2$O, 2:2:1). Analysis. Calc for C$_{21}$H$_{38}$N$_5$O$_3$.2 HCL.2C$_2$H$_5$OH: C, 53.27; H, 7.53; N, 12.43. Found: C, 52.91; H, 7.75; N, 12.80.

The structure and physical characterization of opiates 1-12 is summarized on Table II, below.

TABLE II

| Compound No. | Formula I (Z=OH) R | R' | Yield % | mp. °C. | R$_f$ | Empirical Formula | Elem. Anal |
|---|---|---|---|---|---|---|---|
| 1 | CH$_2$CH(CH$_2$)$_2$ | COCH$_2$CH$_2$COOH | 85 | 245-248 | 0.22$^a$ | C$_{24}$H$_{30}$N$_2$O$_6$.0.75H$_2$O | C, H, N |
| 2 | " | CO(CH$_2$)$_3$COOH | 62 | >260 | 0.43$^b$ | C$_{25}$H$_{32}$N$_2$O$_6$.C$_2$H$_4$O$_2$.0.5H$_2$O | |
| 3 | " | H<br>COC=CCOOH<br>H | 86 | >280 | 0.25$^a$ | C$_{24}$H$_{28}$N$_2$O$_6$.H$_2$O | C, H, N |
| 4 | " | COCH$_2$OCH$_2$COOH | 75 | >250 | 0.40$^c$ | C$_{24}$H$_{30}$N$_2$O$_7$.2H$_2$O | C, H, N |
| 5 | " | COCH(NH$_2$)(CH$_2$)$_3$NHC(NH)NH$_2$ | 70 | >280 | 0.12$^d$ | C$_{26}$H$_{39}$N$_6$O$_4$.5HCl | C, H, N |
| 6 | " | COCH(NH$_2$)CH$_2$COOH | 71 | >280 | 0.18$^d$ | C$_{24}$H$_{31}$N$_3$O$_6$.2.3HCl.2H$_2$O | C, H, N, Cl |
| 7 | " | CH$_2$COOH | 66 | >280 | 0.15$^d$ | C$_{22}$H$_{28}$N$_2$O$_5$.3H$_2$O | C, H, N |

TABLE II-continued

| Compound No. | Formula I (Z=OH) R | Formula I (Z=OH) R' | Yield % | mp. °C. | $R_f$ | Empirical Formula | Elem. Anal |
|---|---|---|---|---|---|---|---|
| 8 | CH₃ | COCH₂CH₂COOH | 64 | 218–220 | 0.15[e] | $C_{21}H_{26}N_2O_6 \cdot 1.5H_2O$ | C, H |
| 9 | " | COC=CCOOH (H cis) | 79 | >280 | 0.27[f] | $C_{21}H_{24}N_2O_6 \cdot 2H_2O$ | C, H, N |
| 10 | " | COC≡CCOOH (H H) | 67 | 294–296 | 0.24[g] | $C_{21}H_{24}N_2O_6 \cdot 1.5H_2O$ | C, H, N |
| 11 | " | COCH₂OCH₂COOH | 47 | 240–242 | 0.14[e] | $C_{21}H_{26}N_2O_7 \cdot 1.5H_2O$ | C, H |
| 12 | " | COCH(NH₂)CH₂COOH | 75 | >280 | 0.05[e] | $C_{21}H_{27}N_3O_6 \cdot 2HCl \cdot 2H_2O$ | C, H, N |

[a] EtOAc—MeOH—H₂O—NH₄OH (75:20:5:2).
[b] CH₃CN—H₂O—HOAc (83:17:3).
[c] EtOAc—MeOH—NH₄OH (70:30:2).
[d] nBuOH—HOAc—H₂O (4:1:1).
[e] EtOAc—MeOH—NH₄OH (50:50:5).
[f] EtOAc—MeOH—NH₄OH (70:30:4).
[g] EtOAc—MeOH—NH₄OH (50:50:1).

EXAMPLE 10

Evaluation of Agonist and Antagonist Activity

Compounds 1–15 were evaluated for biological activity with respect to electrically-stimulated guinea pig ileum (GPI) preparations by the method of H. B. Rang, Brit. J. Pharmacol., 22, 356 (1964). The concentration-response-relationship for agonism was compared to that of morphine, which was run as a control for each preparation. The antagonist potency was evaluated by the displacement of the morphine concentration-response curve to higher concentration in the presence of the antagonist. These values are expressed as a ratio of $IC_{50}$ values ($IC_{50}$ of morphine in the presence of the antagonist divided by the control $IC_{50}$ of morphine). The agonist and antagonist data obtained are summarized on Table III, below.

TABLE III

Agonist and Antagonist Activities on the Guinea Pig Ileum Preparation.

| Compound | Agonism[a] (Morphine = 1) | Antagonism[b] (Morphine IC₅₀ Ratio)[c] |
|---|---|---|
| 1 | d | 11.0 |
| 3 | 3 | 3.7[e] |
| 4 | d | 34.8 |
| 5 | d | 4.0 |
| 6 | 14.2 | 1 |
| 7 | d | 2.4[e] |
| 8 | 1.6 | 1 |
| 9 | 1.5 | 1 |
| 10 | 2.7 | 1 |
| 11 | 3.1 | 1 |
| 12 | 6.1 | 1 |
| 15 | d | 100 |
| 16 | 29 | f |

[a] Potency factors for the inhibition of contraction of the electrically stimulated guinea pig ileum relative to that of morphine (3 determinations).
[b] Unless otherwise stated, the concentration of the ligand was 200 nM.
[c] The factor by which the morphine concentration-response curve is shifted in a parallel fashion to higher concentration in the presence of the ligand (3 determinations).
[d] Partial agonist; maximal response at 1 uM was 30–60% that of morphine.
[e] Ligand concentration = 20 nM.
[f] Unable to measure antagonism due to potent agonism.

All of the oxymorphamine derivatives 8–12 were determined to be more potent than morphine in inhibiting contraction of the GPI. It is likely that many of these compounds will possess substantial antidiarrheal activity. No morphine antagonist activity was observed with these compounds.

The naltrexamine derivatives 1–7 generally were observed to function as morphine antagonists. The aspartyl compound 6 was a possible exception to this generality. All of these compounds (1–7) possessed agonist activity, but 1, 4, 5 and 7 produced submaximal responses relative to morphine. These compounds are therefore classified as mixed agonist-antagonists, which may be useful to block the constipation caused by opiate analgesics.

The results of these studies indicate that it is possible to modify the C-6 position of a variety of opiates by introducing ionizable groups without compromising agonist activity. In fact, the N-methyl compounds all were highly potent agonists in the GPI and most of the N-cyclopropyl analogues were capable of shifting the morphine dose-response curves to higher concentration.

The fact that the attachment of polar groups (R') did not adversely affect the primary activity of many of the compounds make them excellent candidates for use in disorders of peripheral origin because access to the CNS would be expected to be substantially reduced from that of the parent unsubstituted agonist and antagonist.

It is apparent that many modifications and variations of this invention may be made without departing from the spirit and scope thereof. The specific embodiments described are given by way of example only and the invention is limited only by the terms of the appended claims.

What is claimed is:

1. A composition of matter of the formula:

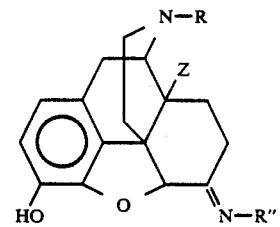

wherein R is (C₁–C₅) alkyl, C₃–C₆(cycloalkyl)alkyl, aryl, aralkyl or trans-(C₂–C₅) alkenyl, Z is H or OH and R″ is NH-A(B)(C) or guanidino, wherein A is selected from the group consisting of (C₁–C₅) alkyl, (C₂–C₅) alkenyl and (C₂–C₅) alkoxy (alkyl); B is selected from the group consisting of H and a (C₁–C₅)alkyl group optionally substituted with CO₂H, OH or phenyl and C is $CO_2H$, $SO_3H$, amino or guanidino; and the pharmaceutically-acceptable salts thereof.

2. The composition of claim 1 wherein R is $C_1$–$C_3$)alkyl, allyl, or cyclopropyl methyl.

3. The composition of claim 1 wherein R" si guanidino or $NH(C_1$–$C_4)alkyl$-$CO_2H$.

4. The composition of claim 1 wherein Z is OH.

UNITED STATES PATENT AND TRADEMARK OFFICE
CERTIFICATE OF CORRECTION

PATENT NO. : 4,730,048
DATED : March 8, 1988
INVENTOR(S) : Philip S. Portoghese

It is certified that error appears in the above-identified patent and that said Letters Patent is hereby corrected as shown below:

At Col. 1, lines 62-63, for "$C_3$-$C_6$ (cycloakyl) alkyl, acryl, aralkyl" read --$C_3$-$C_6$ (cycloalkyl) alkyl, aryl, aralkyl--.

At Col. 4, Table 1, for " " read -- --.

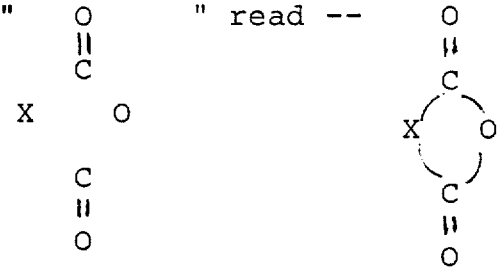

At Col. 6, line 43, for "of 11 or 13" read --of 14 or 13--.

At Col. 12, line 1, claim 3, for "wherein R" si" read --wherein R" is--.

Signed and Sealed this

Twenty-ninth Day of November, 1988

Attest:

DONALD J. QUIGG

Attesting Officer    Commissioner of Patents and Trademarks